US010760074B2

(12) United States Patent
Usui et al.

(10) Patent No.: US 10,760,074 B2
(45) Date of Patent: Sep. 1, 2020

(54) COMPOSITION FOR DETECTION OF RNA

(75) Inventors: Kanako Usui, Otsu (JP); Takashi Uemori, Otsu (JP); Hiroyuki Mukai, Otsu (JP); Ikunoshin Kato, Otsu (JP)

(73) Assignee: TAKARA BIO INC., Kusatsu-Shi (JP)

( * ) Notice: Subject to any disclaimer, the term of this patent is extended or adjusted under 35 U.S.C. 154(b) by 896 days.

(21) Appl. No.: 13/059,703

(22) PCT Filed: Aug. 31, 2009

(86) PCT No.: PCT/JP2009/065151
§ 371 (c)(1),
(2), (4) Date: Feb. 18, 2011

(87) PCT Pub. No.: WO2010/026933
PCT Pub. Date: Mar. 11, 2010

(65) Prior Publication Data
US 2011/0151467 A1  Jun. 23, 2011

(30) Foreign Application Priority Data
Sep. 3, 2008  (JP) .................. 2008-225519

(51) Int. Cl.
C12Q 1/68     (2018.01)
C12N 15/10    (2006.01)
C12Q 1/6848   (2018.01)

(52) U.S. Cl.
CPC ....... *C12N 15/1096* (2013.01); *C12Q 1/6848* (2013.01)

(58) Field of Classification Search
USPC .... 435/91.2, 91.21, 6, 6.12, 69.1, 91.1, 199, 435/91.51, 91.5, 183; 536/24.3, 24.33, 536/23.1, 24.31; 935/77, 78; 3/91.2, 3/91.21, 6, 6.12, 69.1, 91.1, 199, 91.51, 3/91.5, 183
See application file for complete search history.

(56) References Cited

U.S. PATENT DOCUMENTS

| | | | | |
|---|---|---|---|---|
| 5,268,289 A * | 12/1993 | Dahl | ......................... | C12N 9/22 435/183 |
| 5,310,652 A * | 5/1994 | Gelfand | ................ | C12N 9/1252 435/6.11 |
| 5,436,149 A * | 7/1995 | Barnes | ........................... | 435/194 |
| 5,561,058 A * | 10/1996 | Gelfand et al. | .............. | 435/91.2 |
| 5,712,127 A * | 1/1998 | Malek | ................. | C12N 15/1072 435/6.14 |
| 5,853,990 A * | 12/1998 | Winger et al. | ............... | 435/6.18 |
| 5,972,607 A * | 10/1999 | Kondo | ................. | C12Q 1/6865 435/183 |
| 5,981,183 A * | 11/1999 | Takarada | ............. | C12Q 1/6865 435/6.12 |
| 6,251,637 B1 * | 6/2001 | Blusch | ........................ | 435/91.1 |
| 6,303,306 B1 * | 10/2001 | Takarada et al. | ............ | 435/6.12 |
| 7,354,742 B2 * | 4/2008 | Kamme et al. | .............. | 435/91.2 |
| 2004/0038366 A1 * | 2/2004 | Uemori | .................... | C12N 9/22 435/199 |
| 2004/0137451 A1 * | 7/2004 | Sagawa | ................. | C12Q 1/683 435/6.12 |
| 2005/0059000 A1 * | 3/2005 | Sagawa | ................ | C12Q 1/6848 435/6.12 |
| 2006/0019366 A1 * | 1/2006 | Bi | ................................. | 435/199 |
| 2009/0269745 A1 | 10/2009 | Tonoike et al. | | |
| 2009/0269809 A1 * | 10/2009 | Hokazono et al. | .......... | 435/69.1 |
| 2010/0016250 A1 | 1/2010 | Nagata et al. | | |
| 2013/0302794 A1 * | 11/2013 | Li | ......................... | C12Q 1/689 435/6.11 |

FOREIGN PATENT DOCUMENTS

| | | | |
|---|---|---|---|
| JP | 2007-228977 | A | 9/2007 |
| JP | 4022522 | B2 | 10/2007 |
| JP | 2008-17777 | A | 1/2008 |
| JP | 2008-17787 | A | 1/2008 |
| JP | 2009-50217 | A | 3/2009 |
| WO | WO 03/072798 | A2 | 9/2003 |
| WO | WO 03/074696 | A1 | 9/2003 |
| WO | WO 03072798 | A2 * | 9/2003 |
| WO | WO 2007/052765 | A1 | 5/2007 |
| WO | WO 2007/119815 | A1 | 10/2007 |

OTHER PUBLICATIONS

Myers TW, Gelfand DH. Reverse transcription and DNA amplification by a Thermus thermophilus DNA polymerase. Biochemistry. 1991. 30(31):7661-6.*
BcaBESTManual.pdf.*
Maeda et al., Quantitative real-time PCR using TagMan and SYBR Green for Actinobacillus actinomycetemcomitans, Porphyromonas gingivalis, Prevotella intermedia, tetQ gene and total bacteria. FEMS Immunol Med Microbiol. 2003. 39(1):81-6.*
Callison SA, Hilt DA, Jackwood MW. Rapid differentiation of avian infectious bronchitis virus isolates by sample to residual ratio quantitation using real-time reverse transcriptase-polymerase chain reaction. J Virol Methods. Mar. 2005;124(1-2):183-90.*
Qiaquick spin handbook (Mar. 2008).*
Epicentre manual (1993).*

(Continued)

*Primary Examiner* — Gary Benzion
*Assistant Examiner* — Olayinka A Oyeyemi
(74) *Attorney, Agent, or Firm* — Birch, Stewart, Kolasch & Birch, LLP

(57) ABSTRACT

A composition for use in amplifying cDNA synthesized by a reverse transcription reaction and detecting RNA that serves as a template of the reverse transcription reaction, the composition containing a thermostable DNA polymerase, a thermostable ribonuclease H, and an intercalating dye. Since the composition of the present invention can suppress the influences to the nucleic acid amplification reaction by RNA that serves as a template for cDNA synthesis, the composition is useful in the detection of RNA, and more useful in quantification of RNA having a desired sequence by real-time RT-PCR.

11 Claims, 1 Drawing Sheet
Specification includes a Sequence Listing.

(56) References Cited

OTHER PUBLICATIONS

SuperScript First Strand Synthesis System Manual (Invitrogen/Life Technologies) 2003.*
Maeda et al. (2003). FEMS Immunology and Medical Microbiol 39: 81-86.*
Schneeberger et al. (1995) PCR methods Appl. 4: 234-238.*
Wang et al. (2003) Nuc. Acid Research. vol. 31 No. 24 E154: p. 1-8.*
Gasparic M, Cankar K, Zel J, Gruden K. Comparison of different real-time PCR chemistries and their suitability for detection and quantification of genetically modified organisms. BMC Biotechnol. Mar. 6, 2008;8:26.*
Epicentre manual (1995) Hybridase Thermostable RNase H, (also disclosed in U.S. Pat. No. 5,268,289, Dec. 7, 1993), retrieved from http://www.epibio.com on Jan 6, 2013.*
Epicentre manual (2012) E. coli RNase H, retrieved from http://www.epibio.com on Jan. 6, 2013.*
Polumuri SK, Ruknudin A, Schulze DH. RNase H and its effects on PCR. Biotechniques. Jun. 2002; 32(6):1224-5. (Year: 2002).*
Kitabayashi M, Esaka M. Improvement of reverse transcription PCR by RNase H. Biosci Biotechnol Biochem. Nov. 2003; 67(11): 2474-6. (Year: 2003).*
Uemori T, Mukai H, Takeda O, Moriyama M, Sato Y, Hokazono S, Takatsu N, Asada K, Kato I. Investigation of the molecular mechanism of ICAN, a novel gene amplification method. J Biochem. Aug. 2007; 142(2):283-92. Epub Aug. 24, 2007. (Year: 2007).*
Higuchi et al., "Kinetic PCR Analysis: Real-time Monitoring of DNA Amplification Reactions", Bio/Technology, vol. 11, Sep. 1993, pp. 1026-1030.
International Search Report dated Sep. 29, 2009 for International Application No. PCT/JP2009/065151.
Kitabayashi et al., "Improvement of Reverse Transcription PCR by RNase H", Biosci. Biotechnol. Biochem., vol. 67, No. 11, 2003, pp. 2474-2476.
Japanese Office Action for Japanese Application No. 2014-224007, dated May 17, 2016.
Extended European Search Report dated Oct. 31, 2011, for European Application No. 09811459.8.
Harvey et al., "Characterization and applications of CataCleave probe in real-time detection assays", Analytical Biochemistry, vol. 333, 2004, pp. 246-255, XP004573012, (Available online Jul. 20, 2004).
Mukai et al., "Highly Efficient Isothermal DNA Amplification System Using Three Elements of 5'-DNA-RNA-3' Chimeric Primers, RNaseH and Strand-Displacing DNA Polymerase", Journal of Biochemistry, vol. 142, No. 2, 2007, pp. 273-281, XP002661810.

* cited by examiner

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial
<220> FEATURE:
<223> OTHER INFORMATION: Primer to amplify the cDNA fragment of human
      APOE gene.

<400> SEQUENCE: 1
ctgcgttgct ggtcacattc                                                   20

<210> SEQ ID NO 2
<211> LENGTH: 20
<212> TYPE: DNA
<213> ORGANISM: Artificial
<220> FEATURE:
<223> OTHER INFORMATION: Primer to amplify the cDNA fragment of human
      APOE gene.

<400> SEQUENCE: 2
```

```
ctcctgcacc tgctcagaca                                                    20

<210> SEQ ID NO 3
<211> LENGTH: 20
<212> TYPE: DNA
<213> ORGANISM: Artificial
<220> FEATURE:
<223> OTHER INFORMATION: Primer to amplify the cDNA fragment of human
      SOX18 gene.

<400> SEQUENCE: 3
agaacccgga cctgcacaac                                                    20

<210> SEQ ID NO 4
<211> LENGTH: 21
<212> TYPE: DNA
<213> ORGANISM: Artificial
<220> FEATURE:
<223> OTHER INFORMATION: Primer to amplify the cDNA fragment of human
      SOX18 gene.

<400> SEQUENCE: 4
gttcagctcc ttccacgctt t                                                  21

<210> SEQ ID NO 5
<211> LENGTH: 20
<212> TYPE: DNA
<213> ORGANISM: Artificial
<220> FEATURE:
<223> OTHER INFORMATION: Primer to amplify the cDNA fragment of human
      NAT14 gene.

<400> SEQUENCE: 5
cctggtgctg gagatgctga                                                    20

<210> SEQ ID NO 6
<211> LENGTH: 20
<212> TYPE: DNA
<213> ORGANISM: Artificial
<220> FEATURE:
<223> OTHER INFORMATION: Primer to amplify the cDNA fragment of human
      NAT14 gene.

<400> SEQUENCE: 6
gcgaaggaag ccaggacaaa                                                    20
```

COMPOSITION FOR DETECTION OF RNA

TECHNICAL FIELD

The present invention relates to a composition useful for detection of RNA, a method for detecting RNA using the composition, and a kit for detecting RNA.

BACKGROUND ART

Nucleic acid amplification methods, especially Polymerase Chain Reaction (PCR) methods, are techniques of conveniently amplifying a desired nucleic acid fragment in vitro, which have become indispensable experimental methods in wide range of fields of biology, medicine, agriculture, and the like. In addition, a method of accurately quantifying DNA that serves as a template is developed by measuring nucleic acid amplification by PCR with the passage of time utilizing, for example, an intercalating dye (Non-Patent Publication 1). This method is referred to as a real-time PCR method, in the sense of distinguishing with conventionally known quantification PCR.

As the real-time PCR method, aside from the method using an intercalating dye, a method using a FRET (fluorescence resonance energy transfer) oligonucleotide probe has been known. As real-time PCR using the FRET oligonucleotide probe, a method utilizing 5'→3' exonuclease activity of DNA polymerase (Taq Man Probe method), a method using Molecular Beacon probe, a method using two kinds of oligonucleotide probes designed to allow FRET to take place when hybridized to a target nucleic acid (HybriProbe method), and a method utilizing a FRET oligonucleotide probe containing ribonucleotide and a thermostable ribonuclease H (RNase H) (CycleavePCR method, Patent Publication 1), or the like have been known.

PCR methods are also applied to a method for detecting RNA, which is referred to as a Reverse Transcriptase PCR (RT-PCR) method. RT-PCR method is a method of synthesizing a DNA (cDNA) complementary to RNA using a reverse transcriptase having RNA-dependent DNA polymerase activity, in other words, reverse transcription activity, or DNA polymerase also having reverse transcription activity, and subsequently carrying out PCR using this cDNA as a template, thereby specifically amplifying and detecting cDNA derived from RNA. RT-PCR method is not only utilized in cloning of cDNA derived from mRNA or preparation of cDNA library, but also useful as a method of examining an expression state of a specified mRNA. Also, a real-time RT-PCR method in which RT-PCR is applied to real-time PCR enables accurate quantification of mRNA, so that the method is applied to expression analysis of genes or generation of expression profiles.

In RT-PCR, cDNA after the reverse transcription reaction forms a DNA/RNA hybrid with RNA that serves as a template for a reverse transcriptase. Therefore, from the beginning of the development of RT-PCR, cDNA is preferably made into a single strand before PCR by a treatment with an alkali, heat, or an enzyme after the reverse transcription reaction, in order to improve the reactivity of RT-PCR. For example, in a case where RNA that serves as a template has a high GC content, there is a report that it is effective to carry out an enzymatic treatment with ribonuclease H derived from *Escherichia coli* after the reverse transcription reaction (Non-Patent Publication 2).

Patent Publication 1: WO 2003/074696
Non-Patent Publication 1: *Biotechnology* (NY). 1993 September; 11(9): 1026-1030.
Non-Patent Publication 2: *Biosci Biotechnol Biochem.* 2003 November; 67(11): 2474-2476.

DISCLOSURE OF THE INVENTION

Problems to be Solved by the Invention

In RT-PCR, if a treatment with an alkali, heat, or an enzyme is carried out after the reverse transcription reaction, a longer time period is required up to the termination of the reaction, as compared to cases where these treatments are not carried out. In addition, in a case where a treatment is carried out with an alkali or an enzyme, a step of adding an alkali or an enzyme to a reverse transcription reaction mixture would be necessitated, thereby making the procedures complicated, and also increasing the risks of contamination. Therefore, improvements in these problems have been desired.

An object of the present invention is to provide a reagent for detecting RNA, a method for detecting RNA, and a kit for detecting RNA, which are more excellent than conventional ones.

Means to Solve the Problems

As a result of intensive efforts in order to solve the above problems, the present inventors have surprisingly found that in a nucleic acid amplification reaction using, as a template, cDNA synthesized by reverse transcription reaction with RNA that serves as a template, a nucleic acid amplification reaction can be carried out conveniently, in a high specificity, and in a high efficiency by utilizing a thermostable ribonuclease H. In addition, more surprisingly, the present inventors have found that a thermostable ribonuclease H functions even in the presence of an intercalating dye, and the present invention has been perfected thereby.

A first invention of the present invention relates to a composition for use in amplifying cDNA synthesized by a reverse transcription reaction and detecting RNA that serves as a template of the reverse transcription reaction, the composition containing a thermostable DNA polymerase, a thermostable ribonuclease H, and an intercalating dye. In the first invention of the present invention, the thermostable DNA polymerase is exemplified by a DNA polymerase derived from extreme thermophile. In addition, in the first invention of the present invention, the thermostable ribonuclease H is exemplified by a ribonuclease H derived from extreme thermophile, such as bacteria belonging to the genus *Thermus,* or archaebacteria belonging to the genus *Thermococcus.* The composition of the first invention of the present invention may further contain at least one member selected from the group consisting of at least one oligonucleotide primer, at least one deoxyribonucleotide, and a buffer for reaction.

A second invention of the present invention relates to a method for detecting RNA, including the steps of:
(A) preparing a composition containing a reverse transcriptase, at least one oligonucleotide primer, at least one deoxyribonucleotide, RNA that serves as a template of a reverse transcription reaction;
(B) incubating the composition prepared in the step (A) to synthesize cDNA;
(C) preparing a composition containing the cDNA synthesized in the step (B), a thermostable DNA polymerase, a thermostable ribonuclease H, and an intercalating dye;

(D) carrying out polymerase chain reaction using the composition prepared in the step (C), and amplifying nucleic acids; and (E) measuring a fluorescent signal intensity from the intercalating dye, thereby detecting the nucleic acids amplified in the step (D).

In the second invention of the present invention, the step (E) may be carried out during the polymerase chain reaction in the step (D). In addition, RNA that serves as a template from the signal intensity measured in the step (E) may be quantified.

A third invention of the present invention relates to a kit for detecting RNA, the kit containing a thermostable DNA polymerase, a thermostable ribonuclease H, and an intercalating dye. The thermostable DNA polymerase and the thermostable ribonuclease H in the third invention of the present invention are exemplified by the same ones as those exemplified in the first invention of the present invention. The kit of the third invention of the present invention may further contain at least one member selected from the group consisting of a reverse transcriptase, at least one primer, at least one deoxyribonucleotide, and a buffer for reaction.

Effects of the Invention

According to the present invention, a reagent for detecting RNA, a method for detecting RNA, and a kit for detecting RNA, each having a shorter operating time and capable of detecting with simplified procedures, and having excellent reactivity, as compared to conventional ones, are provided.

Figure 1:
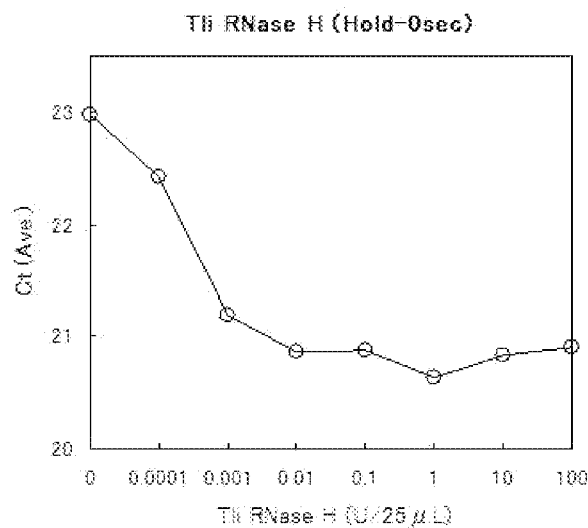
FIG. 1 A graph showing the relationship between RNase H level in a reaction mixture for PCR and Ct value.

BEST MODE FOR CARRYING OUT THE INVENTION (1) Composition of the Present Invention The composition of the present invention contains a thermostable DNA polymerase, a thermostable ribonuclease H, and an intercalating dye.

In addition, a composition containing a thermostable DNA polymerase and a thermostable ribonuclease H, but without containing an oligonucleotide probe containing a ribonucleotide, is also one embodiment of the present invention. The composition of this embodiment is useful in real-time RT-PCR using a FRET oligonucleotide probe, a method of confirmation by electrophoresing an amplified product obtained by RT-PCR, or the like.

The reactivity of the nucleic acid amplification reaction is not particularly limited. In PCR, the reactivity can be confirmed by a thermal cycle number (Ct value) at a time when an amount of nucleic acid amplification in PCR reaches a certain amount. For example, when the reactivities of two different the nucleic acid amplification reaction systems are compared, if Ct values are confirmed by carrying out nucleic acid amplification reactions of each of the reaction systems with a template of the same amount, the one with a lower Ct value can be regarded as a nucleic acid amplification reaction system having a higher reactivity.

The thermostable DNA polymerase as used herein refers to a DNA-dependent DNA polymerase that keeps an activity even after 30 minutes of a treatment at a temperature of 75° C. or higher. The thermostable DNA polymerase may further have a 5'→3' exonuclease activity, a 3'→5' exonuclease activity, and/or a RNA-dependent DNA polymerase activity.

The thermostable DNA polymerase used in the present invention may be any of those that can be used in PCR, and already many kinds have been made commercially available. The thermostable DNA polymerase used in the present invention is exemplified by a DNA polymerase derived from extreme thermophile, without particularly limiting the present invention thereto. The extreme thermophile refers to a bacterium that is capable of growing even under the environmental conditions of 75° C. or higher. The extreme thermophiles include, for example, eubacteria such as eubacteria belonging to the genus *Thermus*, such as *Thermus aquaticus*, *Thermus thermophilus*, *Thermus flavus*, and *Thermus filiformis*; and archaebacteria such as archaebacteria belonging to the genus *Pyrococcus*, such as *Pyrococcus furiosus*, *Pyrococcus woesei*, and *Pyrococcus horikoshii*, and archaebacteria belonging to the genus *Thermococcus*, such as *Thermococcus litoralis*, *Thermococcus celer*, *Thermococcus siculi*, *Thermococcus* sp. KS-1, and *Thermococcus kodakaraensis*. Here, as the thermostable DNA polymerases in the present invention, a mixture of two or more kinds of thermostable DNA polymerases may be used.

The ribonuclease H refers to a hydrolase that cleaves specifically only RNA-chain of a DNA/RNA hybrid in the endo-form, which may be also expressed as RNase H. The thermostable ribonuclease H as used herein refers to a ribonuclease H that keeps an activity even after a treatment at a temperature of 60° C. or higher for 15 minutes.

The thermostable ribonuclease H in the present invention is exemplified by a ribonuclease H derived from extreme thermophile, without being particularly limited thereto, and more preferably exemplified by a ribonuclease H derived from bacteria belonging to the genus *Thermus*, such as *Thermus thermophilus* or *Thermus flavus*; and a ribonuclease H derived from archaebacteria belonging to the genus *Thermococcus*, such as *Thermococcus litoralis*. WO 02/22831 also discloses a thermostable ribonuclease H.

The intercalating dye refers to a dye that enhances fluorescence by the intercalation to a double-stranded nucleic acid. For example, ethidium bromide, SYBR (registered trademark) Green I, PicoGreen, SYTO9, SYTO13, EvaGreen, YOYO, TOTO, and these analogues, and the like are utilized in intercalating dyes for real-time PCR. The intercalating dye in the present invention is exemplified by the above-mentioned dyes, without being particularly limited thereto. The intercalating dye in the present invention embraces any dyes so long as the dye enhances fluorescence by intercalation to a nucleic acid.

The composition of the present invention may contain, in addition to the thermostable DNA polymerase, the thermostable ribonuclease H, and the intercalating dye, at least one oligonucleotide primer, at least one deoxyribonucleotide, and/or a buffer for reaction.

The oligonucleotide primers (also simply referred to as primers) are not particularly limited so long as the oligonucleotide primers are oligonucleotides that anneal to a nucleic acid or a primer extension strand on the side of a complementary side that serves as a template in the operating reaction conditions. The primer has a chain length of preferably 6 nucleotides or more, and more preferably 10 nucleotides or more, from the viewpoint of carrying out specific annealing, and the primer has a chain length of preferably 100 nucleotides or less, and more preferably 30 nucleotides or less, from the viewpoint of synthesis of the oligonucleotide. The above-mentioned oligonucleotide can be synthesized by, for example, a phosphoramidite method using a DNA synthesizer model 394 from ABI (Applied Biosystem Inc.). Besides the above, the oligonucleotide may be synthesized by any methods such as phosphate triester method, H-phosphonate method, and thiophosphonate method. In addition, the oligonucleotide may be an oligonucleotide derived from a biological sample, or may be, for example, prepared by isolation from a restriction endonuclease digest of DNA prepared from a naturally occurring sample.

The deoxyribonucleotide is a product in which phosphate group is bound to an organic base-bonded deoxyribose via a phosphoester bonding. The naturally occurring DNA contains 4 kinds of nucleotides. Each of nucleotides having adenine, guanine, cytosine, and thymine bases is embraced in naturally occurring DNA. The bases adenine, guanine, cytosine, and thymine are very often abbreviated by A, G, C, and T, respectively.

The deoxyribonucleotide includes monophosphate-forms, diphosphate-forms, and triphosphate-forms of deoxyribonucleoside (in other words, the phosphate moiety has one, two, or three phosphate groups). Therefore, the deoxyribonucleotide includes deoxyribonucleoside triphosphates (for example, dATP, dCTP, dITP, dGTP and dTTP) and derivatives thereof. Preferably, a composition containing four kinds of deoxyribonucleotides, which are dATP, dCTP, dGTP and dTTP, is used in the present invention.

The deoxyribonucleotide derivative includes [αS]dATP, 7-Deaza-dGTP, 7-Deaza-dATP, and a deoxynucleotide derivative showing resistivity to nucleolytic degradation. The nucleotide derivative includes, for example, labeled deoxyribonucleotides so as to be detectable with a radioisotope such as $^{32}P$ or $^{35}S$, a fluorescent moiety, a chemoluminescent moiety, a bioluminescent moiety, or an enzyme. These deoxyribonucleotide derivatives may be added to the composition of the present invention, as occasion demands, or may be substituted with a deoxyribonucleotide corresponding to the above-mentioned naturally occurring DNA.

The buffer for the reaction refers to a solution containing one or more buffer components for adjusting a pH of the reaction mixture, which may further contain a divalent cation and a monovalent cation. The buffer for the reaction may contain, in addition to the above-mentioned components, a detergent or a component for improving the activity and stability of the thermostable DNA polymerase and/or the thermostable ribonuclease H.

The method for preparing a composition of the present invention is not particularly limited. Concretely, a composition can be prepared by mixing a thermostable ribonuclease H and at least one oligonucleotide primer with a mixture containing a thermostable DNA polymerase, an intercalating dye, and optionally at least one deoxyribonucleotide, and a buffer for reaction. Here, as a mixture containing a thermostable DNA polymerase, an intercalating dye, a deoxyribonucleotide, and a buffer for reaction, a commercially available product such as SYBR (registered trademark) Premix Ex Taq™ (Perfect Real Time) (manufactured by TAKARA BIO INC.) can be suitably used.

One embodiment of the composition of the present invention includes a concentrated-form composition in which each of the components is formulated so as to have a concentration appropriate for PCR by adding a template DNA to a composition of the present invention, and diluting the solution with a sterile distilled water or the like upon use. According to this embodiment, a reaction mixture for nucleic acid amplification can be conveniently prepared.

(2) Method of the Present Invention

The method for detecting RNA of the present invention includes the steps of:
(A) preparing a composition containing a reverse transcriptase, at least one oligonucleotide primer, at least one deoxyribonucleotide, and RNA that serves as a template;
(B) incubating the composition prepared in the step (A) to synthesize cDNA;
(C) preparing a composition containing the cDNA synthesized in the step (B), a thermostable DNA polymerase, a thermostable ribonuclease H, and an intercalating dye;
(D) carrying out polymerase chain reaction using the composition prepared in the step (C), and synthesizing nucleic acids; and
(E) measuring a fluorescent signal intensity from the intercalating dye, thereby detecting the nucleic acids synthesized in the step (D).

The reverse transcriptase in the above-mentioned step (A) can be used in the present invention so long as the reverse transcriptase has reverse transcription activity, in other words, an activity of synthesizing a DNA complementary to RNA that serves as a template, and the reverse transcriptase as described above is exemplified by reverse transcriptases derived from viruses, such as reverse transcriptase derived from Moloney murine leukemia virus (reverse transcriptase derived from MMLV), and reverse transcriptase derived from avian myeloblastosis virus (reverse transcriptase derived from AMV); thermostable reverse transcriptases derived from eubacteria, such as DNA polymerase derived from bacteria belonging to the genus *Thermus* (Tth DNA polymerase or the like), and DNA polymerase derived from thermophilic bacteria belonging to the genus *Bacillus* (Bca DNA polymerase or the like). A commercially available reverse transcriptase may be also used.

In the method of the present invention, the reverse transcriptases derived from viruses are preferably used, and the reverse transcriptase derived from MMLV is more preferably used. In addition, a reverse transcriptase in which a wild-type amino acid sequence is subjected to a modification within the range so as to have a reverse transcription activity can be also used in the present invention.

The RNA that serves as a template is RNA that can act, when a primer is annealed, as a template of a reverse transcription reaction from the primer. The composition prepared in the step (A) may contain one kind of template RNA or plural kinds of templates having different nucleotide sequences. cDNA complementary to the above template can be prepared by using primers specific to a particular template RNA. When primers capable of annealing to plural template RNAs are selected, primer extension products for plural kinds of templates in a nucleic acid mixture can be prepared. The plural templates may exist in different nucleic acids or in the same nucleic acid.

The RNA that serves as a template which can be applied to the present invention is not particularly limited, and includes any kinds of RNA in a sample, in other words RNA molecules such as mRNA, tRNA, and rRNA, or specified RNA molecules (for example, RNA molecules having a common nucleotide sequence motif, transcripts by RNA polymerases, and RNA molecules concentrated by subtraction method), and includes any RNAs capable of designing primers usable in the reverse transcription reaction.

In the present invention, the RNA that serves as a template may be contained in samples possibly containing organisms, such as samples from live bodies, such as cells, tissue, and blood, foods, soils and wastewater, or may be contained in a nucleic acid-containing preparation mixture obtained by treating the samples or the like by a known method. The preparation mixture includes, for example, cell disruptions or samples obtained by fractionation thereof, total RNA in the sample, or specified RNA molecules, for example, samples rich in mRNA, and the like.

A method for preparing a composition for carrying out the reverse transcription reaction, in other words, a reaction mixture for reverse transcription, is well known to one of ordinary skill in the art, and a reaction mixture containing various components mentioned above in proper concentrations may be prepared. A reaction mixture for reverse transcription can be easily prepared if a commercially available kit for reverse transcription is used.

In the step (B) according to the method mentioned above, a cDNA complementary to a template RNA is synthesized. The conditions for incubation in the step (B) are not particularly limited, and the temperature conditions are, for example, from 30° to 65° C., and more preferably from 37° to 45° C. Also, the reaction time is, for example, from 5 to 120 minutes, and more preferably from 15 to 60 minutes. The above-mentioned conditions may be properly adjusted depending upon the amounts of the reverse transcriptase and the template RNA.

In the step (C) according to the method mentioned above, a composition containing the cDNA synthesized in the step (B), a thermostable DNA polymerase, a thermostable ribonuclease H, and an intercalating dye is prepared. The thermostable DNA polymerase, the thermostable ribonuclease H, and the intercalating dye are exemplified by those described in (1) "Composition of the Present Invention" mentioned above, and the composition may be prepared by mixing a composition of the present invention with the cDNA synthesized in the step (B).

In the step (D) according to the method mentioned above, polymerase chain reaction is carried out using the composition prepared in the step (C), with the cDNA synthesized in the step (B) as a template, thereby amplifying nucleic acids. PCR according to the method of the present invention may be PCR with a thermal cycle in which one cycle consists of three-stage temperatures, or shuttle PCR with a thermal cycle in which one cycle consists of two-stage temperatures. PCR may be carried out in, for example, thermal cycles consisting of 20 to 50 cycles.

In addition, before the three-stage or two-stage thermal cycles mentioned above, a heat treatment of 90° C. or more for 15 seconds to 10 minutes may be provided. In PCR with cDNA synthesized by reverse transcription reaction as a template, it is preferable that a heat treatment is carried out before the thermal cycles of PCR, from the viewpoint of improvement in reactivity. Surprisingly, in a case where a composition of the present invention is used in PCR with cDNA that serves as a template, the amplification efficiency for PCR in which the heat treatment is carried out before the thermal cycles for PCR mentioned above is further improved.

In the step (E) according to the method mentioned above, a fluorescent signal intensity from the intercalating dye is measured, thereby detecting the nucleic acids amplified in the step (D). By this step, RNA that serves as a temple for amplified nucleic acids can be detected. The fluorescent signal from the intercalating dye is illuminated by irradiating an excitation light of the intercalating dye to a reactive composition, and its intensity increases with an increase of the amount of the double-stranded nucleic acids. The detection of the fluorescent signal intensity may be carried out after the PCR reaction, or may be carried out for each thermal cycle of the reaction for PCR in the step (D). By measuring a fluorescent signal intensity from an intercalating dye for each thermal cycle of reaction for PCR, it is made possible to quantify an amount of a template cDNA for PCR, and it is further made possible that an amount of RNA that serves as a template for amplified cDNA is determined from the amount of cDNA quantified. Therefore, the method for detecting RNA of the present invention may further include (F) the step of quantifying RNA that serves as a template from the signal intensity measured in the step (E).

In the measurement of the fluorescent signal intensity in the reaction for PCR, for example, a commercially available equipment for real-time PCR may be used. The commercially available equipments for real-time PCR is exemplified by Thermal Cycler Dice (registered trademark) Real Time System (manufactured by TAKARA BIO INC.), and Smart Cycler (registered trademark) II System (manufactured by TAKARA BIO INC.).

(3) Kit of the Present Invention

The kit of the present invention is a kit for detecting RNA, the kit containing a thermostable DNA polymerase, a thermostable ribonuclease H, and an intercalating dye. The kit of the present invention allows to efficiently carry out nucleic acid amplification reaction in which cDNA synthesized by reverse transcription reaction serves as a template, so that it is useful in the detection of RNA having a desired sequence, and that it is more useful in quantification of RNA having a desired sequence.

The kit of the present invention may contain, in addition to the thermostable DNA polymerase, the thermostable ribonuclease H, and the intercalating dye, at least one oligonucleotide primer, at least one deoxyribonucleotide, and/or a buffer for reaction.

The thermostable DNA polymerase, the thermostable ribonuclease H, the intercalating dye, at least one oligonucleotide primer, at least one deoxyribonucleotide, and/or the buffer for reaction may be contained in the kit in the state where a part or all of these components are mixed, or each of these components may be contained in the kit in a single component state. For example, a mixture of a thermostable DNA polymerase, an intercalating dye, at least one deoxyribonucleotide, and a buffer for reaction includes commercially available products such as SYBR (registered trademark) Premix Ex Taq™ (Perfect Real Time) (manufactured by TAKARA BIO INC.), and the like.

In addition, the kit of the present invention may further contain a reagent for carrying out reverse transcription reaction. The reagent as mentioned above includes a reverse transcriptase, at least one oligonucleotide primer, at least one deoxyribonucleotide, and/or a buffer for reaction. Here, the primer as referred to herein includes those that are preferably used in reverse transcription, without particular limitation.

The thermostable DNA polymerase, the thermostable ribonuclease H, the intercalating dye, the reverse transcriptase, at least one oligonucleotide primer, at least one deoxyribonucleotide, and the buffer for reaction contained in the kit of the present invention are exemplified by those described in (1) "Composition of the Present Invention" or (2) "Method of the Present Invention" mentioned above.

Since the composition of the present invention can suppress influences to nucleic acid amplification reaction by RNA that serves as a template of cDNA synthesis, the composition is useful in the detection of RNA, and further may be used for carrying out quantification by detecting RNA. Also, the composition is more useful in quantification by real-time RT-PCR of RNA having a desired sequence.

EXAMPLES

The present invention will be specifically described hereinbelow by the Examples, without intending to limit the present invention to the scope of Examples. Here, unless specified otherwise, the activity of each enzyme in the following Examples is shown on the basis of the indication of the attached manual to each enzyme.

Example 1

(1) Synthesis of cDNA from RNA

Reverse transcription reaction was carried out utilizing PrimeScript (registered trademark) RT reagent Kit (Perfect Real Time) (manufactured by TAKARA BIO INC., Product Code: RR037A) with Human Testis Total RNA (manufactured by Clontech) as a template, in accordance with the standard protocol of the manufactured article to prepare cDNA.

(2) Amplification and Detection of cDNA

As the real-time PCR apparatus, Thermal Cycler Dice (registered trademark) Real Time System (manufactured by TAKARA BIO INC.) was used. An Apolipoprotein E (APOE) gene was amplified and detected by using SYBR (registered trademark) Premix Ex Taq™ (Perfect Real Time) (manufactured by TAKARA BIO INC., Product Code: RR041), with a 20 ng portion of the cDNA obtained by reverse transcription reaction as a template. Concretely, as a reaction mixture for amplification and detection of cDNA, to 20 ng of cDNA obtained in (1) was added a mixture prepared by adding 10 pmol of APOE-F primer having a nucleotide sequence shown in SEQ ID NO: 1 of Sequence Listing, 10 pmol of APOE-R primer having a nucleotide sequence shown in SEQ ID NO: 2 of Sequence Listing, and sterile distilled water, and further adding 0.0001 U, 0.001 U, 0.01 U, 0.1 U, 1 U, 10 U, or 100 U ribonuclease H derived from *Thermococcus litralis* (hereinafter referred to as Tli RNase H, prepared in accordance with the description of WO 02/22831) to a premix reagent in a 2× concentration that attached to Premix Ex Taq™ (Perfect Real Time), to prepare 7 kinds of reaction mixtures (25 μL each) each having a different content of Tli RNase H. In addition, a reaction mixture having the same composition as the reaction mixture mentioned above except for not containing Tli RNase H was prepared (25 μL in total). The eight (8) kinds of reaction mixtures were subjected to 40 cycles of PCR, wherein one cycle of reaction consists of first stage: 95° C. for 5 seconds, second stage: 60° C. for 30 seconds (n=2). At this time, a fluorescent intensity from SYBR (registered trademark) Green I was measured for each cycle of PCR, and a change in the levels of amplified products was observed. After the termination of reaction, a Ct value calculated by Crossing Point method in Auto set-up with a real-time apparatus was confirmed, and an average was obtained.

(3) Results

The calculated Ct values are shown in Table 1. Also, the relationship between RNase H level in a reaction mixture for PCR and Ct value is shown in the graph of FIG. 1.

TABLE 1

| Tli RNaseH [U/25 μL] | Ct Value (1) | Ct Value (2) | Average |
| --- | --- | --- | --- |
| 0 | 23.00 | 22.94 | 22.97 |
| 0.0001 | 22.40 | 22.45 | 22.43 |
| 0.001 | 21.18 | 21.20 | 21.19 |
| 0.01 | 20.91 | 20.83 | 20.87 |
| 0.1 | 20.88 | 20.89 | 20.89 |
| 1 | 20.62 | 20.66 | 20.64 |
| 10 | 20.81 | 20.86 | 20.84 |
| 100 | 20.90 | 20.92 | 20.91 |

As a result, as compared to a case where RNase H was not added, a reaction mixture containing Tli RNase H has a low Ct value. It was clarified from the above that amplification efficiency is improved by adding thermostable RNase H in a reaction mixture during PCR with cDNA synthesized by reverse transcription reaction as a template.

Example 2

As to a case where heat denaturation was carried out before the PCR nucleic acid amplification using the same apparatus and reagents as in Example 1, it was also confirmed that a Ct value lowers by adding RNase H.

To 10 ng of cDNA prepared in the same manner as in Example 1(1) was added a mixture prepared by adding 10 pmol of APOE-F primer, 10 pmol of APOE-R primer, and sterile distilled water, and further adding 1 U Tli RNase H to a premix reagent in a 2× concentration that attached to Premix Ex Taq™ (Perfect Real Time), to prepare a reaction mixture for amplification and detection of APOE gene fragment in a total of 25 μL. In addition, the same procedures as above were carried out except that SOX-F primer having a nucleotide sequence shown in SEQ ID NO: 3 of the Sequence Listing and SOX-R primer having a nucleotide sequence shown in SEQ ID NO: 4 of the Sequence Listing were used in place of the APOE-F primer and the APOE-R primer, to prepare a reaction mixture for amplifying and detecting Sex-Determining Region Y Box 18 (SOX18) gene fragment. Similarly, NAT-F primer having a nucleotide sequence shown in SEQ ID NO: 5 of the Sequence Listing and NAT-R primer having a nucleotide sequence shown in SEQ ID NO: 6 of the Sequence Listing were used in place of the APOE-F primer and the APOE-R primer, to prepare a reaction mixture for amplifying and detecting N-acetyltransferase 14 (NAT14) gene fragment. In addition, a reaction mixture for amplification and detection of each target sequence having the same composition as each of the above reaction mixtures, except for not containing 1 U Tli RNase H was prepared.

For each of the six (6) reaction mixtures mentioned above, amplification efficiency in a case where heat denaturation is not carried out before PCR and a case where heat denaturation is carried out before PCR was confirmed. In the case where a heat denaturation is not carried out before the reaction for PCR, a reaction mixture was subjected to 40 cycles of PCR wherein one cycle consists of first stage: 95° C. for 5 seconds, and second stage: 60° C. for 30 seconds. In the case where a heat denaturation is carried out before the reaction for PCR, a reaction mixture was subjected to a heat denaturation treatment for 95° C. for 30 seconds, and thereafter to 40 cycles of PCR wherein one cycle consists of first stage: 95° C. for 5 seconds, and second stage: 60° C. for 30 seconds (each n=1). During PCR, a fluorescent intensity from SYBR (registered trademark) Green I was measured for each cycle, and a change in the levels of amplified products was observed. After the termination of reaction, a Ct value calculated by Crossing Point method in Auto set-up with a real-time apparatus was confirmed. The calculated Ct values are shown in Table 2.

TABLE 2

| | Ct Values | | | |
|---|---|---|---|---|
| | No Heat Denaturation Before PCR | | Heat Denaturation Before PCR | |
| Target Gene | RNase H (−) | RNase H (+) | RNase H (−) | RNase H (+) |
| APOE | 24.32 | 22.15 | 23.49 | 21.87 |
| SOX18 | 30.22 | 28.64 | 29.97 | 28.33 |
| NAT14 | 33.72 | 30.74 | 31.43 | 28.56 |

As a result, even in a case where heat denaturation was carried out before the reaction for PCR, it could be seen that reaction efficiency is further improved by adding RNase H. From these results, it was evident that a thermostable RNase H in the reaction mixture for PCR exhibits effects even in a case where DNA/RNA hybrid formed between cDNA after reverse transcription reaction and RNA that served as a template for reverse transcription reaction is eliminated before nucleic acid amplification reaction by heat denaturation.

Example 3

The same procedures for amplification and detection of cDNA as in Example 1 were carried out except that Hybridase™ Thermostable RNase H (hereinafter referred to as Hybridase, manufactured by Epicentre, thermostable RNase H derived from bacteria belong to the genus *Thermus*) was used in place of Tli RNaseH, that RNase H levels per 25 μL of a reaction mixture were 0.0001 U, 0.001 U, 0.01 U, 0.1 U, and 1 U, and an initial denaturation at 95° C. for 30 seconds was carried out before PCR to confirm a Ct value.

Figure 2:
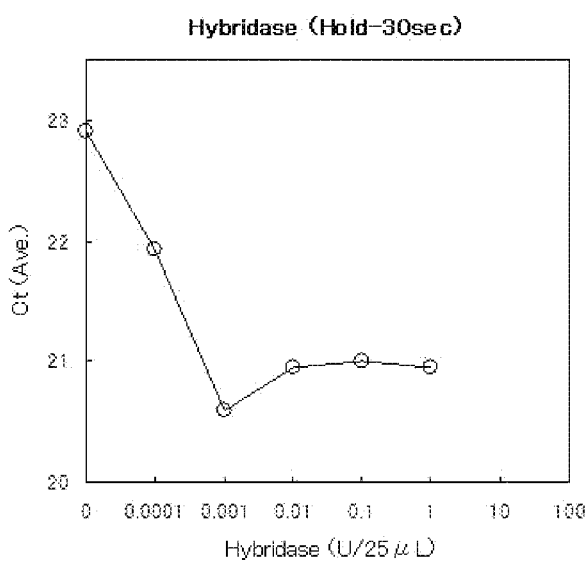
FIG. 2 A graph showing the relationship between RNase H level in a reaction mixture for PCR and Ct value.

The calculated Ct values are shown in Table 3. Also, the relationship between RNase H level in a reaction mixture for PCR and Ct value is shown in the graph of FIG. 2.

TABLE 3

| Hybridase [U/25 μL] | Ct Value (1) | Ct Value (2) | Average |
|---|---|---|---|
| 0 | 22.85 | 22.95 | 22.90 |
| 0.0001 | 21.99 | 21.86 | 21.93 |
| 0.001 | 20.60 | 20.58 | 20.59 |
| 0.01 | 21.02 | 20.88 | 20.95 |
| 0.1 | 21.06 | 20.94 | 21.00 |
| 1 | 20.98 | 20.91 | 20.95 |

As a result, in a case where a thermostable RNase H derived from the bacteria belonging to the genus *Thermus* was used, improvement in nucleic acid amplification efficiency by the addition of RNase H was found.

INDUSTRIAL APPLICABILITY

The composition, the method for detecting RNA using the composition, and the kit for detecting RNA of the present invention are widely useful in the field of genetic engineering. In particular, since the influences to the nucleic acid amplification reaction by RNA that serves as a template for cDNA synthesis can be suppressed according to the present invention, the present invention is useful in the detection of RNA, and more useful in quantification of RNA having a desired sequence by real-time RT-PCR.

SEQUENCE LISTING FREE TEXT

SEQ ID NO: 1; Primer to amplify the cDNA fragment of human APOE gene.
SEQ ID NO: 2; Primer to amplify the cDNA fragment of human APOE gene.
SEQ ID NO: 3; Primer to amplify the cDNA fragment of human SOX18 gene.
SEQ ID NO: 4; Primer to amplify the cDNA fragment of human SOX18 gene.
SEQ ID NO: 5; Primer to amplify the cDNA fragment of human NAT14 gene.
SEQ ID NO: 6; Primer to amplify the cDNA fragment of human NAT14 gene.

The invention claimed is:

1. A method for detecting RNA, comprising the steps of:
   (A) preparing a first composition comprising a reverse transcriptase, at least a first oligonucleotide primer, at least one deoxyribonucleotide, and RNA that serves as a template of a reverse transcription reaction;
   (B) incubating the first composition prepared in the step (A) to synthesize cDNA, wherein the cDNA after the reverse transcription reaction forms a DNA/RNA hybrid with RNA that serves as a template for a reverse transcriptase;
   (C) preparing a second composition comprising the cDNA synthesized in the step (B), a thermostable DNA polymerase, a thermostable ribonuclease H, wherein the thermostable ribonuclease H is contained in the second composition at a concentration of 0.001 to 100 U/25 μL, at least a second oligonucleotide primer, at least one deoxyribonucleotide, a buffer for polymerase chain reaction, and an intercalating dye;
   (D) carrying out a heat treatment of the second composition prepared in the step (C) at 90° C. or more for 15 seconds to 10 minutes, and carrying out polymerase chain reaction using the product obtained by the heat treatment, and amplifying nucleic acids; and
   (E) measuring a fluorescent signal intensity from the intercalating dye, thereby detecting the nucleic acids amplified in the step (D).

2. The method according to claim 1, wherein the step (E) is carried out during the polymerase chain reaction in the step (D).

3. The method according to claim 1 or 2, further comprising the step (F) of quantifying RNA that serves as a template from the signal intensity measured in the step (E).

4. The method according to claim 1, wherein the thermostable ribonuclease H is contained in the second composition at a concentration of 0.01 to 10 U/25 μL.

5. The method according to claim 1, wherein the thermostable ribonuclease H is contained in the second composition at a concentration of 0.1 to 10 U/25 μL.

6. The method according to claim 1, wherein the thermostable ribonuclease H is contained in the second composition at a concentration of 0.1 to 1 U/25 μL.

7. The method according to claim 1, wherein the thermostable ribonuclease H is selected from a ribonuclease H from bacteria belonging to the genus *Thermus* or *Thermococcus*.

8. A method for detecting RNA, comprising the steps of:
(A) preparing a composition comprising a DNA/RNA hybrid, a thermostable DNA polymerase, a thermostable ribonuclease H, at least one oligonucleotide primer, at least one deoxyribonucleotide, a buffer for polymerase chain reaction, and an intercalating dye,
(B) subjecting the composition prepared in step (A) to polymerase chain reaction continuously with heat treatment at 90° C. or more for 15 seconds to 10 minutes to amplify the nucleic acid, and
(C) detecting the nucleic acid amplified in step (B) by measuring the intensity of the fluorescent signal from the intercalating dye,
wherein the thermostable DNA polymerase is selected from the group consisting of *Thermus aquaticus, Thermus thermophiles, Thermus flavus, Thermus filiformis, Pyrococcus furiosus, Pyrococcus woesei, Pyrococcus horikoshii, Thermococcus litoralis, Thermococcus celer, Thermococcus siculi, Thermococcus* sp. KS-1 and *Thermococcus kodakaraensis;* and
wherein the thermostable ribonuclease H is selected from the group consisting of *Thermus thermophiles, Thermus flavus* and *Thermococcus litoralis*.

9. The method according to claim 8, wherein step (C) is carried out during the polymerase chain reaction in the step (B).

10. The method according to claim 8, further comprising the step (D) of quantifying RNA that serves as a template from the signal intensity measured in the step (C).

11. The method according to claim 9, further comprising the step (D) of quantifying RNA that serves as a template from the signal intensity measured in the step (C).

* * * * *